(12) United States Patent
MacGregor

(10) Patent No.: US 7,381,424 B2
(45) Date of Patent: Jun. 3, 2008

(54) HYDROSTATIC DELIVERY SYSTEM FOR CONTROLLED DELIVERY OF AGENT

(76) Inventor: Alexander MacGregor, 34 White Avenue, Scarborough, Ontario M1C 1P2 (CA)

( * ) Notice: Subject to any disclaimer, the term of this patent is extended or adjusted under 35 U.S.C. 154(b) by 0 days.

(21) Appl. No.: 10/006,740

(22) Filed: Dec. 5, 2001

(65) Prior Publication Data

US 2002/0155067 A1    Oct. 24, 2002

Related U.S. Application Data

(60) Provisional application No. 60/251,751, filed on Dec. 5, 2000.

(51) Int. Cl.
*A61K 9/46* (2006.01)
*A61K 9/00* (2006.01)
*A61K 47/32* (2006.01)

(52) U.S. Cl. .................. 424/466; 424/43; 424/400; 424/484; 514/772.4

(58) Field of Classification Search ............ 514/772.4; 424/78.01, 472
See application file for complete search history.

(56) References Cited

U.S. PATENT DOCUMENTS

| | | | |
|---|---|---|---|
| 2,909,462 A | 10/1959 | Warfield et al. | 167/56 |
| 3,033,754 A | 5/1962 | Krahnke et al. | 167/82 |
| 3,042,667 A | 7/1962 | Flodin et al. | 260/209 |
| 3,208,994 A | 9/1965 | Flodin et al. | 260/209 |
| 3,330,729 A | 7/1967 | Johnson, Jr. | 167/82 |
| 3,458,622 A | 7/1969 | Hill | 424/19 |
| 3,459,850 A | 8/1969 | Riva | 424/22 |
| 3,538,214 A | 11/1970 | Shoop et al. | 424/19 |
| 3,845,770 A | 11/1974 | Theeuwes et al. | 128/260 |
| 3,916,899 A | 11/1975 | Theeuwes et al. | 128/260 |
| 4,002,173 A | 1/1977 | Manning et al. | 128/296 |
| 4,248,857 A | 2/1981 | DeNeale et al. | 424/21 |
| 4,601,894 A | 7/1986 | Hanna et al. | 424/19 |
| 4,624,847 A | 11/1986 | Ayer et al. | 424/15 |
| 4,654,393 A | 3/1987 | Mikita et al. | 526/240 |
| 4,680,323 A | 7/1987 | Lowey et al. | 524/43 |
| 4,687,757 A | 8/1987 | Parrott et al. | 502/220 |
| 4,954,562 A | 9/1990 | Anderson | 524/779 |

(Continued)

FOREIGN PATENT DOCUMENTS

EP    0486863    5/1992

(Continued)

OTHER PUBLICATIONS

Bruck, S.D., "Pharmacological Basis of Controlled Drug Delivery," Chapter 1 In *Controlled Drug Delviery vol. 1 Basic Concepts*, Bruck, S. (Ed.) Boca Raton, LA: CRC Press, Inc., 1983 pp. 1-13.

(Continued)

*Primary Examiner*—Michael G. Hartley
*Assistant Examiner*—Blessing M Fubara
(74) *Attorney, Agent, or Firm*—Arent Fox LLP

(57) ABSTRACT

The present invention provides a hydrostatic delivery system comprising a hydrostatic couple and an agent of interest. The hydrostatic couple comprises, at least one hydrodynamic fluid-imbibing polymer, and at least one hydrostatic pressure modulating agent. This delivery system has the ability to control the release of one or more agent of interest within a fluid environment following zero-order kinetics.

11 Claims, 6 Drawing Sheets

U.S. PATENT DOCUMENTS

| | | | |
|---|---|---|---|
| 4,994,276 A | | 2/1991 | Baichwal et al. ............ 424/440 |
| 5,082,668 A | | 1/1992 | Wong et al. ................. 424/473 |
| 5,213,794 A | * | 5/1993 | Fritsch et al. ............ 424/78.01 |
| 5,357,636 A | * | 10/1994 | Dresdner et al. ............. 2/161.7 |
| 5,456,921 A | | 10/1995 | Mateescu et al. ........... 424/465 |
| 5,582,838 A | * | 12/1996 | Rork et al. ................. 424/472 |
| 5,780,057 A | * | 7/1998 | Conte et al. ................ 424/468 |
| 5,807,575 A | | 9/1998 | Dumoulin et al. .......... 424/464 |
| 5,840,329 A | * | 11/1998 | Bai ............................ 424/458 |
| 6,071,539 A | * | 6/2000 | Robinson et al. ........... 424/466 |
| 6,200,604 B1 | * | 3/2001 | Pather et al. ............... 424/466 |

FOREIGN PATENT DOCUMENTS

| | | |
|---|---|---|
| GB | 0905000 | 5/1962 |
| WO | 0245695 | 6/2002 |

OTHER PUBLICATIONS

Dressman, J.B., "Physiological Aspects of the Design of Dissolution Tests," In: *Scientific Foundations for Regulating Drug Product Quality* Amidon, G.L. et al. (Eds.), AAPS Press, 1997 pp. 155-168.

Rippie, E.TG., "Mixing," In: *The Theory and Practice of Industrial Pharmacy* Lachman, L. et al. (Eds.), Philadelphia, PA: Lea & Febiger, 1986 pp. 3-20.

Rutenberg, M.W. and D. Solarek, "Starch Derivatives: Production and Uses," Chapter X In: *Starch Chemistry and Technology*, 2nd ed., Whistler, R.L. et al. (Eds.), Orlando, FLA: Academic Press, 1984 pp. 311-388.

Ueno, N. and M.F. Refojo et al., "Ocular Pharmacology of Drug Release Devices," Chapter 4 In: *Controlled Drug Delivery vol. II Clinical Applications*, Bruck, S. (Ed.) Boca Raton, FLA: CRC Press, Inc., 1983 pp. 89-109.

Khan, et al., "Formumlation and in vitro evaluation of ibuprofen-carbopol 974P-NF controlled release matrix tablets III: influence of co-excipients on release rate of the drug," *J. Controlled Release* 54:185-190 (1998).

Dorkoosh, et al., "Preparation and NMR characterization of superorous hydrogels (SPH) and SPH composites," *Polymer* 41:8213-8220 (2000).

* cited by examiner

HYDROSTATIC DELIVERY SYSTEM FOR CONTROLLED DELIVERY OF AGENT

RELATED APPLICATIONS

This application claims benefit of priority under 35 U.S.C. §119(e) to U.S. provisional application Ser. No. 60/251,751, filed Dec. 5, 2000, to Alexander MacGregor, entitled "HYDROSTATIC DELIVERY SYSTEM FOR CONTROLLED DELIVERY OF AGENT". The subject matter of the provisional application is incorporated herein in its entirety.

FIELD OF INVENTION

The present invention relates to a delivery system for the controlled release of an agent of interest, as well as compositions and methods of preparation of the delivery system. More particularly, the present invention provides a hydrostatic pressure-activated delivery system for dispensing an agent of interest to an environment of use.

BACKGROUND OF THE INVENTION

The clinical advantages of controlled and patterned delivery of therapeutic agents are well established in the art. Many of the desirable attributes of controlled release pharmaceutical preparations stem from their ability to deliver predetermined quantities of one or more active agent(s) with a high degree of precision over a desired time frame.

Delivery devices and systems for the controlled release of active agents are generally characterized as either diffusion controlled delivery systems; erosion controlled systems, osmotic dispensing devices, or combinations of diffusion and erosion control. These devices and systems are derived from various compositions and techniques such as matrix processes, core embedding processes, coating processes as well as osmotically activated processes. Exemplifying these delivery devices are a broad range of systems from time release capsules whose contents have coatings that erode at different rates, diffusion-controlled matrix tablets with hydro-swellable barriers, and controlled release-rate tablets which operate by osmosis. Irrespective of the mechanism underlying the controlled release of an agent of interest, it is desired that a delivery system be characterized by a constant and reproducible in-vivo pharmacokinetic response facilitated by zero-order release kinetics (i.e. where the release of an agent of interest, for example a pharmaceutical agent, is independent of its own concentration).

U.S. Pat. Nos. 4,601,894, 4,687,757, 4,680,323, 4,994,276 disclose controlled release delivery devices based on matrix systems. These matrix systems are generally known to lack the ability to release pharmaceutical agents according to zero-order kinetics. (e.g. S. D. Bruck, *Controlled Drug Delivery*, Vol. I and II, CRC Press (1983)).

Core embedding or core coated delivery systems have been disclosed, for example in U.S. Pat. No. 3,538,214. This document describes a diffusion-controlled device in which a tablet core containing the active ingredient, is surrounded by a water insoluble coating. The insoluble film coating has been modified with modifying agents that are soluble to the external fluids in the gastrointestinal tract.

U.S. Pat. Nos. 3,845,770 and 3,916,899 disclose osmotic devices comprising a core composition of an active agent in combination with an osmotically effective solute, that is enclosed by an insoluble semi-permeable wall having a release capacity. The release characteristics of these devices have been improved through modifications disclosed, for example, in U.S. Pat. Nos. 4,624,847, 5,082,668, In principle, osmotic delivery employs one or more osmotic pressure adjuvants, for example a salt, and one or more components involved in expansion, for example a polymer, to deliver an agent of interest to a fluid environment over a period of time. The osmotic pressure adjuvants present in the delivery device are used to cause the influx of water by osmosis, through a semi-permeable wall, while the component involved with expansion absorbs liquid, expands, and acts to drive out the agent of interest from the interior of the osmotic device in a controlled and constant manner. Such systems are capable of zero-order release kinetics.

A disadvantage with coated delivery systems as well as osmotic devices, is that any damage to the wall or shell results in the premature release of the pharmaceutical agent within a short period of time causing what is known in the art as "dose dumping". Patient safety is jeopardized as a result of side effects and possible toxicity from high levels of an agent of interest, for example a pharmacological agent, being released within the blood stream over a short period of time.

While attempts have been made to minimize the safety risks associated with conventional single unit delivery devices by developing multiple unit osmotic pumps, these embellishments have led to increased manufacturing costs (e.g. S. D. Bruck, supra). Similarly, osmotic delivery systems typically comprise one or more openings for the passage of an agent from the delivery device to the environment. The manufacture of the openings within the delivery device may be carried out using one or more laser drills (e.g. U.S. Pat. Nos. 3,845,770 and 3,916,899). The additional steps and machines required for the manufacture of fixed openings within the delivery device also increase the cost of manufacture of such delivery devices.

While delivery systems have been designed that reduce the risk levels to the patient, there still remains significant and inherent shortcomings in osmotic devices, in part due to their reliance on the need for an osmotic gradient to be established between the contents of the device and the fluid environment as well as the need for fixed opening(s) for the delivery of the agent. A blockage of the opening(s) either during storage or handling prior to patient consumption or due to the imminent interaction with dietary contents such as solid food particulate, or simply due to adherence to the gastrointestinal cell wall, will alter the osmotic gradient and severely impair the performance of the osmotic device.

In addition, fluctuating osmolarity in the environment of use, such as the human gastro-intestinal tract, impacts on the reproducibility and performance of osmosis-dependent devices. It is well known that the osmolarity of human gastrointestinal fluid is imminently variable in the fed and fasted states. There can be a substantial increase of up to two fold in the fed state within the individual (J. B. Dressman, *Physiological Aspects of the Design of Dissolution Tests, Scientific Foundation for Regulating Drug Product Quality*—AAPS Press 1997). These natural variables are further pronounced by diets containing varying salt and electrolyte contents. The performance of osmotically driven delivery devices is dependant upon many physiological variables and the dietary habits of patients. For example, side effects within patients (the "flame-cutter effect") arising from the concentrated release of a pharmaceutical agent from the release opening(s) of osmotic systems has led to the withdrawal of preparations comprising Indomethacin.

Additionally, some active agents posses chemical properties that are comparable in ionic strengths to those of strong electrolytes and salts commonly used as osmotic adjuvants. In these instances, and due to different pH environments in the gastrointestinal tract, agents comprising significant ionic strength will manifest varying degrees of ionization that may compromise the predictable performance of the osmotic device. Osmotically active therapeutic agents with ionic strengths comparable to that of osmotic adjuvants, and that are localized within osmotically driven devices, will act as osmotic agents and enhance the osmotic influx of water from the fluid environment. Similarly, agents having high ionic strength may also cause variations in the osmolarity of the adjacent fluid environment upon their release from the delivery device. Therefore, osmotically-driven devices comprising agents characterised as having a high ionic strength, lack self-regulation.

A delivery system that is not readily influenced by minor changes to its physical form, intrinsic properties of an active agent (e.g. ionic strength), or variables in the environment of use (e.g. varying osmolarity of the human gastrointestinal tract and factors such as the dietary contents), can be reliably programmed to deliver the agent in a pre-determined manner with increased accuracy and precision. therefore, there remains within the art a need for a reliable zero-order drug delivery system, where the release of an agent is independent of its own concentration, that provides controlled drug delivery of an active agent to an environment of use and that is independent of physiological variables of the environment of use, as well as the intrinsic properties of the active agent.

It is an object of the invention to overcome disadvantages of the prior art.

The above object is met by the combinations of features of the main claims, the sub-claims disclose further advantageous embodiments of the invention.

SUMMARY OF THE INVENTION

The present invention relates to a delivery system for the controlled release of an agent of interest, as well as compositions and methods of preparation of the delivery system. More particularly, the present invention provides a hydrostatic pressure-activated delivery system for dispensing an agent of interest to an environment of use.

According to the present invention there is provided a hydrostatic delivery system comprising a hydrostatic couple and an agent of interest.

The present invention pertains to a hydrostatic delivery system comprising a hydrostatic couple comprising at least one hydrodynamic fluid-imbibing polymer, and at least one hydrostatic pressure modulating agent. Preferably, the hydrodynamic fluid-imbibing polymer is a cross-linked polymer with a swelling capacity in a fluid environment of between about 1 weight % to about 3000 weight %. Preferably, the cross-linked polymer is present from about 4 weight % to about 96 weight % of the total formulation. Also, it is preferred that the hydrostatic pressure modulating agent is a cross-linked, rapidly swelling polymer with a swelling capacity in a fluid environment of between about 0.5 weight % to about 500 weight %. Preferably the cross-linked, rapidly swelling polymer is present from about 1 weight % to about 50 weight % of the total formulation.

This invention further embraces a hydrostatic delivery system as defined above, wherein the hydrodynamic polymer and the hydrostatic pressure modulating agent are present at a ratio from about 99:1 to about 50:50 by weight.

The present invention also provides for the hydrostatic delivery system as defined above wherein the hydrostatic pressure modulating agent further comprises an expansion source, selected from the group consisting of a carbon-dioxide precursor, an oxygen precursor, and a chlorine dioxide precursor. Preferably, when the hydrodynamic polymer comprises a carbon dioxide precursor, oxygen precursor or chlorine dioxide precursor, the hydrodynamic polymer and the hydrostatic pressure modulating agent are present in a ratio from about 99:1 to about 70:30 by weight.

According to the present invention, a hydrostatic delivery system is provided as defined above, comprising a hydrodynamic fluid-imbibing polymer selected from the group consisting of:

i) an acrylic-acid polymer cross-linked with allylsucrose or allylpentaerythritol;

ii) one or more starch derivatives cross-linked by Epichlorhydrin, Phosphorous oxychloride ($POCl_3$), or Sodium trimetaphosphate;

iii) a polyglucan;

iv) a crosslinked polyacrylate resin;

v) a crosslinked polyethylenimine;

vi) a crosslinked polyallylamine, and combinations thereof, and a hydrostatic pressure modulating agent selected from the group consisting of:

i) homopolymers of cross-linked N-vinyl-2-pyrollidone;

ii) a rapidly expanding cross-linked cellulose derivative; and combinations thereof.

The present invention also provides for the hydrostatic delivery system as defined above, wherein the dosage form is a multiparticulate matrix tablet, or capsule. The hydrostatic delivery system may also comprising an enteric coating or one or more pH sensitive barrier polymers. The hydrostatic delivery system may be:

i) a matrix-type solid compact, made by a compression or pelletization, a matrix-type extrusion spheroid, made by a wet or dry extrusion;

ii) be granulated or microencapsulated to form particulates that may be compressed into solid compacts or filled into capsules; or iii) spheroidal, compact, comprising dry blends, filled into capsules or suspended in a suitable liquid vehicle.

The present invention also embraces the hydrostatic delivery system as defined above, wherein the agent of interest is selected from the group consisting of analgesic, anti-inflammatory, antimicrobial, amoebicidal, trichomonocidal agents, anti-parkinson, anti-malarial, anticonvulsant, anti-depressants, antiarthritics, anti-fungal, antihypertensive, antipyretic, anti-parasite, antihistamine, alpha-adrenargic agonist, alpha blocker, anesthetic, bronchial dilator, biocide, bactericide, bacteriostat, beta adrenergic blocker, calcium channel blocker, cardiovascular drug, contraceptive, decongestants, diuretic, depressant, diagnostic, electrolyte, hypnotic, hormone, hyperglycemic, muscle relaxant, muscle contractant, ophthalmic, parasympathomimetic, psychic energizer, sedative, sympathomimetic, tranquilizer, urinary, vaginal, viricide, vitamin, non-steroidal anti-inflammatory, angiotensin converting enzyme inhibitors, polypeptide, proteins, and sleep inducers.

This summary of the invention does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein.

DESCRIPTION OF PREFERRED EMBODIMENT

Figure 1:
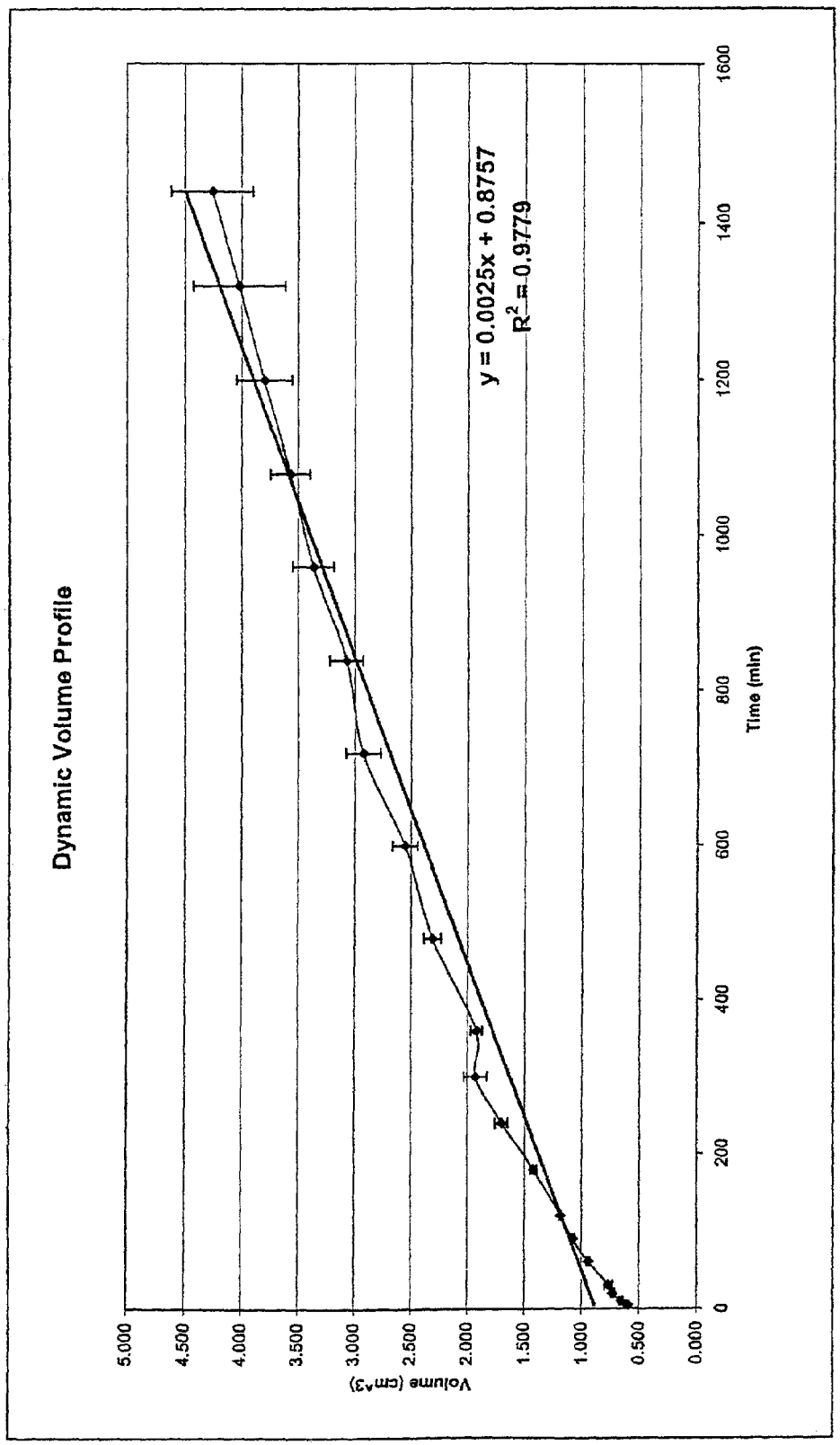
FIG. 1 shows the change in dynamic profile of a prior art delivery system.

The present invention relates to a delivery system for the controlled release of an agent of interest, as well as compositions and methods of preparation of the delivery system. More particularly, the present invention provides a hydrostatic pressure-activated delivery system for dispensing an agent of interest to an environment of use.

The following description is of a preferred embodiment by way of example only and without limitation to the combination of features necessary for carrying the invention into effect.

As used herein, the term "hydrodynamic fluid-imbibing polymer" means any polymer, synthetic or otherwise, that absorbs water or any fluid composition, in part by capillarity with a corresponding dynamic increase in volume and mass. By "capillarity" it is meant the passage of solvent into a solid polymer, for example a hydrodynamic fluid-imbibing polymer, as a result of differential pressure within the pore structure of the polymer and the fluid environment. Capillary uptake by the polymer is initiated by wetting and is dependent on the surface tension of the fluid and structural composition of the polymer.

As described in more detail below, and without wishing to be bound by theory, when two different intimately mixed fluid-imbibing polymers are compacted and exposed to a fluid environment such as water or biological fluid, the mixture of fluid imbibing polymers will absorb the fluid according to the individual contribution and propensity for water imbibition of the component polymers. If the rates and extents of fluid absorption are substantially different for the two polymers, and provided that the rate of volume expansion is greater for the polymer in lower concentration within the mixture, a differential dynamic volume expansion results. Such differential expansion essentially creates an internal stress that will ordinarily disrupt the compact causing complete disintegration. If the polymer present in larger molar concentration within the mixture is cross-linked thereby creating a microporus structure, the microporous structure of the polymer network offers a resistance to the internal stress from the other rapidly expanding polymer. This resistance creates a positive hydrostatic differential pressure that increases the efflux of imbibed fluid to the external media. Under these conditions the volume of the mixture of the fluid-imbibing polymers continues to increase at a diminishing rate determined by the hydrostatic pressure driven fluid efflux. At a given point the rates of volume increase will equal the rate of volume efflux and a dynamic steady state develops whereby the volume change is negligible. The dynamic steady state proffers a constant volume and surface area for both fluid influx and efflux. The delivery system operating on these principles is capable of controlling the release of both soluble and poorly soluble agents of interest by effectively changing the rate of volume efflux through hydrostatic pressure modulation. The hydrostatic pressure of the delivery system may be increased by adding an expansion source, for example a mixture of alkaline and acidic agent as described below.

As used herein, "hydrostatic delivery system" refers to a composition that controls the release of an agent of interest contained therein, using non-osmotic hydrostatic differential pressure.

By "agent of interest" and "beneficial agent" it is meant one or more compounds or mixture of compounds that can be released from the delivery system of the present invention to produce a desired or beneficial result. The agent of interest can be soluble in the fluid that is imbibed by the delivery system or it can have limited solubility in the imbibed fluid and be mixed with an effective solubilizer to enhance its solubility or a suitable excipient to retard its solubility. The agent of interest can be in the delivery system in form of solid particles, granules, microencapsulated solid, microencapsulated liquid, powder and coated particles, for example, the agent of interest may comprise a plurality of discrete active particulates. Water insoluble agents of interest can be used in form that renders it water soluble and upon release from the delivery system, is converted to its original, or biologically active form, by enzyme hydrolysis, by pH, or a metabolic processes depending on the environment of use.

Examples of beneficial agents are disclosed in Remington's Pharmaceutical Sciences (16th Ed., 1980, published by Mack Publishing Co., Easton, Pa.; and in The Pharmacological Basis of Therapeutics, by Goodman and Gilman, 6th Ed., 1980, published by The MacMillian Company, London). Furthermore, an agent of interest may be selected from the following compounds, however, it is to be understood that the following compounds is not meant to be exhaustive. Many other agents of interest will certainly work in the hydrostatic delivery system of this invention. For example, agents of interest include, but are not limited to, pesticides, herbicides, germicides, biocides, fungicides, algicides, insecticides, rodenticides, antioxidants, preservatives, plant growth inhibitors, plant growth promoters, chemical reactants, disinfectants, sterilization agents, foods, fermentation agents, food supplements, cosmetics, nutrients, vitamins, pharmaceutical drugs, nutraceuticals, vitamins, sex sterilants, fertility promoters, fertility inhibitors, microorganism attenuators, air purifiers, or other agents that benefit the environment of their use. By "drug", it is meant any therapeutically or pharmacologically active substances that produce a localized or systemic effect or effects in animals, for example, but not limited to mammals, humans and primates. The expression "drug formulation" as used herein means the drug, by itself or the drug along with other excipients in an intimate mixture with a hydrostatic couple as described herein.

Therapeutic or pharmacologically active substances also include, but are not limited to, analgesic, anti-inflammatory, antimicrobial, amoebicidal, trichomonocidal agents, antiparkinson, anti-malarial, anticonvulsant, anti-depressants, antiarthritics, anti-fungal, antihypertensive, antipyretic, antiparasite, antihistamine, alpha-adrenargic agonist, alpha blocker, anesthetic, bronchial dilator, biocide, bactericide, bacteriostat, beta adrenergic blocker, calcium channel blocker, cardiovascular drug, contraceptive, decongestants, diuretic, depressant, diagnostic, electrolyte, hypnotic, hormone, hyperglycemic, muscle relaxant, muscle contractant, ophthalmic, parasympathomimetic, psychic energizer, sedative, sympathomimetic, tranquilizer, urinary, vaginal, viricide, vitamin, non-steroidal anti-inflammatory, angiotensin converting enzyme inhibitors, polypeptide, proteins, sleep inducers.

Other agents of interest include, but are not limited to, organic and inorganic compounds in various forms, such as charged molecules, molecular complexes, pharmacologically acceptable salts such as hydrochlorides, hydrobromides, palmitate, phosphate, sulphate laurylate, nitrate, borate, maleate, tartrate, acetate, salicylate and oleate. Prodrugs and derivatives of drugs such as esters, ethers and amides.

An agent of interest also includes drugs that act on the peripheral nerves, for example, but not limited to, adrenergic receptors, cholinergic receptors, nervous system, skeletal muscles, cardiovascular, smooth muscles, blood circulatory system, synoptic sites, neuroeffector junctional sites, endocrine and hormone systems, immunological system, reproductive system, skeletal system, autocoid systems, alimentary and excretory systems, inhibitory of autocoids and histamine systems, those materials that act on the central nervous system such as hypnotics and sedatives, including pentobarbital sodium, phenobarbital, secobarbital, thiopental and mixtures thereof; heterocyclic hypnotics such as dioxopiperidines and glutarimides; hypnotics and sedatives such as amides and ureas, exemplified by diethylisovaleramide and .alpha. -bromoisovaleryl urea; hypnotic and sedative urethanes and disulfanes; psychic energizers such as isocoboxazid, nialamide, phenelzine, imipramine, amitryptyline hydrochloride, tranylcypromine and pargylene; and protryptyline hydrochloride, tranquilizers such as chloropromazine, promazine, fluphenzaine, reserpine, deserpidine, meprobamate, and benzodiazepines such as chlordiazepoxide; anticonvulsants such as primidone, enitabas, diphenylhydantion, ethyltion, pheneturide and ethosuximide; muscle relaxants and antiparkinson agents such as mephenesin, methocarbomal, cyclobenzaprine trihexylphenidyl, levodopa/carbidopa, and biperiden; antihypertensives such as .alpha.-methyldopa and L-.beta.-3-4-dihydroxyphenylalanine, and pivaloyloxyethyl ester of .alpha.-methyldopa hydrochloride dihydrate; analgesics such as morphine, codeine, meperidine, nalorphine; antipyretics and anti-inflammatory agents such as aspirin, indomethacin, sodium indomethacin trihydrate salicylamide, naproxen, colchicine, fenoprofen, sulindac, diflunisal, diclofenac, indoprofen and sodium salicyl-amide; local anesthetics such as procaine, lidocaine, maepaine, piperocaine, tetracaine and dibucane; antispasmodics and muscle contractants such as atropine, scopolamine, methscopolamine, oxyphenonium, papaverine; prostaglandins such as $PGE_1$, $PGE_2$, $PGF_1$ alpha., $PGF_2$ alpha. and PGA; antimicrobials and antiparasitic agents such as penicillin, tetracycline, oxytetracycline, chloro-tetracycline, chloramphenicol, thiabendazole, ivermectin, and sulfonamides; antimalarials such as 4-aminoquinolines, 8-aminoquinolines and pyrimethamine; hormonal agents such as dexamethasone prednisolone, cortisone, cortisol and triamcinolone; androgenic steroids such as methyltestosterone, and fluoxmesterone; estrogenic steroids such as 17.beta.-estradiol, .alpha.-estradiol, estriol, alpha.-estradiol 3-benzoate, and 17-ethynyl estradiol-3-methyl ether; progestational steroids such as progesterone, 19-nor-pregn-4-ene-3, 20-dione, 17-hydroxy-19-nor-17-.alpha.-pregn-5(10)-ene-20-yn-3-one, 17. alpha.-ethynyl17-hydroxy-5(10)-estren-3-one, and 9.beta., 10. alpha.-pregna-4,6-diene-3,20-dione; sympathomimetic drugs such as epinephrine, phenylpropoudamine hydrochloride, amphetamine, ephedrine and norepinephrine; hypotensive drugs such as hydralazine; cardiovascular drugs such as procainamide, procainamide hydrochloride, amyl nitrite, nitroglycerin, dipyredamole, sodium nitrate and mannitol nitrate; diuretics such as chlorathiozide, acetazolamide, methazolamide, hydrochlorothiazide, amiloride hydrochloride and flumethiazide, ethacrynic acid, furosemide; antiparasitics such as bephenium, hydroxynaphthoate, dichlorophen and dapsone; and neoplastics such as mechlorethamine, uracil mustard, 5-fluorouracil, 6-thioguanine and procarbazine; beta. -blockers such as pindolol, propranolol, practolol, metoprolol, oxprenolol, timolol, timolol maleate, atenolol, alprenolol, and acebutolol; hypoglycemic drugs such as insulin, isophane insulin, protamine zinc insulin suspension, globin zinc insulin, extended insulin zinc suspension toblutamide, acetohexamide, tolazamide and chlorpropamide; antiulcer drugs such as cimetidine; nutritional agents such as ascorbic acid, niacin, nicotinamide, folic acid, choline, biotin, pantothenic acid, and vitamin B.sub. 12; essential amino acids; essential fats; eye drugs such as timolol, timolomaleate, pilocarpine, pilocarpine salts such as pilocarpine nitrate, pilocarpine hydrochloride, dichlorphenamide, atropine, atropine sulfate, scopolamine and eserine salicylate; histamine receptor antagonists such as cimetidine; and electrolytes such as calcium gluconate, calcium lactate, potassium chloride, potassium sulfate, sodium chloride, potassium fluoride, sodium fluoride, ferrous lactate, ferrous gluconate, ferrous sulfate, ferrous fumurate and sodium lactate; and drugs that act on alpha.-adrenergic receptors such as clonidine hydrochloride.

Additional agents of interest include quinoline and naphthyridine carboxylic acids and related compounds, such as 1-ethyl-6-fluoro-1,4-dihydro-4-oxo-7-(1-piperazinyl)-3-quinolinecarboxylic acid; 1-ethyl-1,4-dihydro-7-methyl-4-oxo-1,8-naphthyridine-3-carboxylic acid; 5-ethyl-5,8-dihydro-8-oxo-1,3-dioxolo[4,5-g]quinoline-7-carboxylicacid; 8-ethyl-5,8-dihydro-5-oxo-2-(1-piperazinyl)pyrido[2,3-d]pyrimidine-6-carboxylic acid; 9-fluoro-6,7-dihydro-5-methyl-1-oxo-1H,5H-benzo[ij]quinoxolizine-2-carboxylic acid; 1-ethyl-1,4-dihydro-4-oxo-7-(4-pyridinyl)-3-quinolinecarboxylic acid; 1-ethyl-1,4-dihydro-4-oxo-[1,3]dioxolo[4,5-g]cinnoline-3-carboxylicacid; 9-fluoro-3-methyl-10-(4-methyl-1-piperazinyl)-7-oxo-2,3-dihydro-7H-pyrido[1,2,3-de][1,4]benzoxazine-6-carboxylic acid; 1-ethyl-6-fluoro-1,4-dihydro-7-(4-methyl-1-piperazinyl)-4-oxo-1,8-naphthyridine-3-carboxylicacid; 1-ethyl-6-fluoro-1,4-dihydro-7-(1-piperazinyl)-4-oxo-1,8-naphthyridine-3-carboxylic acid; 1-cyclopropane-6-fluoro-1,4-dihydro-4-oxo-7-(1-piperazinyl)-3-quinolinecarboxylic acid; 1-methylamino-6-fluoro-1,4-dihydro-4-oxo-7-(4-methyl-1-ipiperazinyl)-3-quinolinecarboxylic acid; 1-(4-fluoro-1-phenyl)-6-fluoro-1 ,4-dihydro-4-oxo-7-( 1-piperazinyl)-3-quinolinecarboxylic acid; 1-(4-fluoro-1-phenyl)-6-fluoro-1,4-dihydro-4-oxo-7-(4-methyl-1-piperazinyl)-3-quinolinecarboxylic acid; 1-(4-fluoro-1-phenyl)-6-fluoro-1,4-dihydro-4-oxo-7-(1-piperazinyl)-1,8-naphthyridine-3-carboxylic acid; and 1-ethyl-6-fluoro-1,4-Dihydro-4-oxo-7-(3-ethylaminomethyl-1-pyrrolidinyl)-8-fluoro-3-quinolinecarboxylic acid.

Additional agents of interest include drugs which affect the respiratory tract such as, but not limited to, budesonide, enprofylline, tranilast, albuterol, theophylline, amoniphylline, brompheniramine, chlorpheniramine, promethazine, diphenhydramine, azatadine, cyproheptadine, terbutaline, metaproterenol, and isoproterenol; drugs which are antidepressants such as amiflamine, alaproclate, doxepin, trazedone, maprotiline, zimelidine, fluvoxamine; antipsychotic drugs such as haloperidol, thioridazine, trifluoperazine, MK-0212, and remoxipride; sedative hypnotic and antianxiety drugs such as triazolam, temazepam, chlorazeptate, alprazolam, diazepam, fluorazepam, lorazepam, oxazepam, hydroxyzine, prazepam, meprobamate, butalbital, and chlorzoxazone; antiparkinson drugs such as benztropine and L-647,339; hormonal and steroidal drugs such as conjugated estrogens, diethylstilbesterol, hydroxy progesterone, medroxy progestrone, norethindrone, betamethasone, methylprednisolone, prednisone, thyroid hormone, levothyroxine and MK-0621; antihypertensive and cardiovascular drugs such as isosorbide dinitrate, digoxin, nadolol, disopyramide, nifedipine, quinidine, lidocaine, diltiazam, verapamil, prazosin, captopril, enalapril, lisinopril, metyrosine, felodipine, tocainide, mexiletine, mecamylamine, and metyrosine; diuretic drugs such as spironolactone, chlorthalidone, metolazone, triamterene, methyclothiazide, and indacrinone; antiinflammatory drugs such as ibuprofen, phenylbutazone, tolmetin, piroxicam, melclofenamate, auranofin, flurbiprofen and penicillamine; analgesic drugs such as acetaminophen, oxycodone, hydrocodone, and propoxyphene; antiinfective drugs such as cefoxitin, cefazolin, cefotaxime, cephalexin, nicarbazin, amprolium, ampicillin, amoxicillin, cefaclor, erythromycin, nitrofurantoin, minocyline, doxycycline, cefadroxil, miconazole clotrimazole, phenazopyridine, clorsulon, fludalanine, pentizidone, cilastin, phosphonomycin, imipenem, arprinocid, and foscarnet; gastrointestinal drugs such as bethanechol, clidinium, dicyclomine, meclizine, prochlorperizine, trimethobenzamide, loperamide, ranitidine, diphenoxylate, famotidine, metoclopramide and omeprazole; anticoagulant drugs such as warfarin, phenindione, and anisindione; and other drugs such as trientine, cambendazole, ronidazole, rafoxinide, dactinomycin, asparaginase, nalorphine, rifamycin, carbamezepine, metaraminol bitartrate, allopurinol, probenecid, diethylpropion, dihydrogenated ergot alkaloids, nystatin, pentazocine, phenylpropanolamine, phenylephrine, pseudoephedrine, trimethoprim and mevinolin.

Therefore, the present invention provides for a delivery system comprising a hydrostatic couple in a solid matrix composition, the matrix composition containing one or more agents of interest with or without other pharmaceutical adjuvant(s). This delivery system ensures the release of one or more agents of interest in a controlled manner, with a zero-order or near zero-order release kinetics, over a therapeutically practical time period. The delivery performance of the delivery system is only minimally affected by physiological variables in the gastrointestinal tract of human and animals.

By "hydrostatic couple" it is meant at least two components, for example, but not limited to a group-A component (a hydrodynamic fluid-imbibing polymer) and a group-B component (a hydrostatic pressure modulating agent). Group-A component(s), are derived from at least one fluid-imbibing cross-linked polymer. Group-B components, are derived from at least one rapid expansion source. Typically these components are placed within a matrix composition. When combined, and placed into a desired fluid environment, the two components act in consort to create a positive hydrostatic pressure that controls the release of one or more agents of interest from within the matrix composition to the adjacent environment. Preferably, the group-A component is dynamically permeable to the external fluids and solutes, and the group-B component is a rapidly expanding compound or provides a rapid expansion source upon interaction with the imbibed fluid.

Once liquid imbibition by capillary uptake is initiated it will continue until the entire solid polymer porous network of the matrix has been exhausted. During this process, the polymers as described herein, for example group-A polymers, undergo a dynamic non-limiting volume and mass increase due to a net influx of fluid. A desirable property of the group-A, hydrodynamic fluid-imbibing polymers, is their swelling ability characterized by weak intermolecular cohesive forces between the cross-linked chains when compared to the stronger intermolecular adhesive interaction between the fluid and polymer micropores. Liquid filled micropores are established during this process, thus allowing the diffusive efflux of solutes through these micropores. If enough solvating fluid is present, over time, the hydrodynamic fluid-imbibing polymers may start shedding.

The net influx of fluid in the polymer of this invention is dependent on both the pore size and microstructure of the polymer arrangement. Hydrodynamic polymers of this invention are cross-linked and the polymer molecular weight between crosslinks is indicative of their pore size. Differential hydrostatic pressure, and in consequence capillary uptake of fluid, within a polymer network that has a smaller pore size and or pronounced interpenetrating polymer structure will be greater in comparison to those polymer networks with a large pore size and fewer interpenetrating structures. In aqueous fluids these polymers will exhibit a linear or near-linear increase in volume and percent mass gain.

The fluid-imbibing polymers (group-A) of this invention are preferably cross-linked water insoluble polymers and can be in the state of dry powder, fine particle, granules or microcapsules.

As used herein, "hydrodynamic boundary" refers to any polymer or compound capable of relaxation upon exposure to the fluid media with a fixed and restricted radius of gyration due to, for example, extensive cross-linking. The molecular chains of these polymers are capable of forming insoluble boundaries or micropores containing water molecules sometimes referred in the art as microgels.

In the system of this invention the hydrodynamic boundary polymers are used in a concentration of about 4 to about 96 weight %, preferably about 60 to about 95, weight %, based on the total weight of the dosage unit.

Examples of suitable cross-linked group-A components (hydrodynamic fluid-imbibing polymer) capable of unlimited volume increase that can be used in this invention include but are not limited to:

acrylic-acid polymers with cross-linking derived from allylsucrose or allylpentaerithritol, including water-insoluble acrylic polymer resins. Single compounds or a blend of compounds from this group of polymers include for example, but not limited to Carbopol.RTM.971-P, Carbopol.RTM.934-P, Carbopol.RTM.974P and Carbopol.RTM.EX-507 (GF Goodrich, or any other commercially available brand with similar properties, may be used). Preferably, the acrylic-acid polymers have a viscosity from about 3,000 centipoise to about 45,000 centipoise at 0.5% w/w concentration in water at 25° C., and a primary particle size range from about 3.00 to about 10.00 microns in diameter, as determined by Coulter Counter;

highly cross-linked or lightly cross-linked starch derivatives crosslinked by Epichlorhydrin or Phosphorous oxychloride (POCl$_3$) or Sodium trimetaphosphate are also suitable for use in the hydrostatic delivery system described herein either singly or in blends;

polyglucans such as amylose, dextran, pullulan succinates and glutarates containing diester-crosslinks either singly or in blends;

diether crosslinked polyglucans such as those disclosed in U.S. Pat. Nos. 3,208,994 and 3,042,667 (which are incorporated herein by reference);

crosslinked polyacrylate resins such as, but not limited to, potassium polyacrylate; and water swellable crosslinked polymer compositions of crosslinked polyethylenimine and or crosslinked polyallyamine.

It is further contemplated that mixtures of the above compounds may be used as a group-A component.

Examples of methods of preparation, for example of Carbopol.RTM.934-P,—a polymer of acrylic acid lightly cross-linked with polyallyl ether of sucrose having an average of 5.8 allyl groups per each sucrose molecule, has been disclosed in U.S. Pat. Nos. 2,909,462; 3,033,754; 3,330,729; 3,458,622; 3,459,850; and 4,248,857 (which are incorporated herein by reference). When Carbopol.RTM.971-P is used, the preferred viscosity of a 0.5% w/w aqueous solution is 2,000 centipoise to 10,000 centipoise. More preferably, the viscosity of a 0.5% w/w aqueous solution is 3,000 centipoise to 8,000 centipoise. When Carbopol.RTM.934-P is used, the preferred viscosity of a 0.5% w/w aqueous solution is 20,000 centipoise to 60,000 centipoise, more preferably, the viscosity of a 0.5% w/w aqueous solution is 30,000 centipoise to 45,000 centipoise.

Cross-linked starch derivatives (crosslinked by Epichlorhydrin or Phosphorous oxychloride (POCl.sub.3) or Sodium trimetaphosphate) include high amylose starch containing varying degrees of crosslinking. These compounds and their methods of preparation are known in the art, for example, U.S. Pat. Nos. 5,807,575 and 5,456,921 (which are incorporated herein by reference), and Rutenberg and Solarek (M. W. Rutenberg and D. Solarek, "Starch derivatives: production and uses" in Starch Chemistry and Technology, 2$^{nd}$ Edition, Chapter X, Pages 311-379, R. L. Whistler, J. N. BeMiller and E. F. Paschall, Academic Press, 1984; which is incorporated herein by reference).

Water-insoluble polyglucans such as amylose, dextran, pullulan succinates and glutarates containing diester-crosslinks also exhibit water imbibition properties suited for group-(A) components of this invention. The methods and manufacture of these compounds have been disclosed in U.S. Pat. No. 4,002,173 (which is incorporated herein by reference). These individual polyglucans or blends derived therefrom can be used to satisfy group-(A) component.

Crosslinked polyacrylate resins such as potassium polyacrylate having sufficiently low water content and capable of being powdered can be use in this invention (see U.S. Pat. Nos. 4,654,393 and 4,954,562, which are incorporated herein by reference). These polyacrylate resins are highly water absorbing and insoluble.

As used herein, "hydrostatic pressure-modulating agent" refers to one or more compounds that expand rapidly upon exposure to fluid, for example, a rapid expansion polymer (a group-B component), serve as an expansion source (see below), or a combination of a rapid expansion polymer and an expansion source.

Hydrophilic cross-linked polymers, known in the art, as super disintegrants can exhibit rapid expansion upon exposure to aqueous media. These polymers are capable of rapid capillary uptake of water and a limiting volume expansion. The limited volume expansion is characterized by an intermolecular cohesive force between the polymer molecules that is stronger in comparison to weaker intermolecular adhesive forces, between the solvent molecules and the polymer pore structure. The rate and extent of volume expansion is dependent on the particle size and nature of the polymer cross-links. A polymer with small particle sizes contains fewer cross-links per unit particle and expands faster, but to a lesser extent, in comparison to the same polymer with larger particle sizes. The rate and extent of expansion in these polymers is much faster than their inherent rate and extent of water imbibition.

Examples of rapid expansion polymers suitable as group-B components of this invention include, but are not limited to:

single compounds or combinations derived from cross-linked N-vinyl-2-pyrollidone (PVP) selected from a group of chemically identical polyvinylpolypyrrolidone such as Polyplasdone.RTM.XL, Polyplasdone.RTM.XL-10, Polyplasdone.RTM.INF-10 (International Specialty Products). Prefreably, the cross-linked N-vinyl-2-pyrollidone has a particle size from about 9 microns to about 150 microns; and cross-linked cellulose derivatives selected from a group of hydrophilic compounds such as cross-linked carboxymethyl cellulose (for example croscarmellose), sodium starch glycolate or a combination thereof.

Therefore, the present invention provides a hydrostatic delivery system comprising a hydrostatic couple, wherein the hydrostatic couple comprises at least one hydrodynamic fluid-imbibing polymer, and at least one hydrostatic pressure modulating agent. Preferably, the hydrodynamic fluid-imbibing polymer is a cross-linked polymer with a swelling capacity in a fluid environment of between about 1 weight % to about 3000 weight %. By swelling capacity it is meant the percentage gain in mass as result of water imbibition, for example as determined using:

(Mass at time (t)–Initial Dry Mass)/Initial Mass.

Preferably, the hydrodynamic fluid-imbibing, cross-linked polymer is present from about 4 weight % to about 96 weight % of the total formulation. Furthermore, the hydrostatic pressure modulating agent is preferably a cross-linked, rapidly swelling polymer with a swelling capacity in fluid environment of between about 0.5 weight % to about 500 weight %. Preferably, the cross-linked, rapidly swelling polymer (the hydrostatic pressure modulating agent) is from about 0.5 weight % to about 50 weight % of the total formulation. However, hydrostatic delivery systems comprising greater than 50 weight %, for example, up to 80 weight %, are also contemplated, depending upon the rate of delivery required, and the drug being delivered.

The present invention also pertains to a hydrostatic delivery system comprising a hydrodynamic polymer and a hydrostatic pressure modulating agent, wherein the hydrodynamic polymer and the hydrostatic pressure modulating agent are present at a ratio from about 99:1 to about 1:99. Preferably, the hydrodynamic polymer and the hydrostatic pressure modulating agent are present at a ratio from about 99:1 to about 50:50.

An "expansion source" is a hydrostatic pressure-modulating agent that is able to create a hydrostatic pressure within the hydrostatic delivery system of the present invention. For example, which is not to be considered limiting, an expansion source may be an alkaline agent capable of releasing a gas, or causing a fluid to effervesce, when exposed to a proton source such as an acidic agent or water. In this manner, the alkaline agent can serve as an expansion source capable of creating a hydrostatic pressure within the hydrostatic delivery system of the present invention. The alkaline agent can be carbon dioxide gas precursor, an oxygen gas precursor or a chlorine dioxide gas precursor.

Alkaline agents of this invention can be selected from, but are not limited to, carbon dioxide precursors such as carbonates, sesquicarbonates and hydrogencarbonate salts of potassium, lithium, calcium, sodium, ammonium, L-lysine carbonate, arginine carbonate, sodium glycine carbonate and sodium amino acid carbonate. The alkaline agents can also be obtained from a group of oxygen gas precursor such as, but not limited to, anhydrous sodium perborate, effervescent perborate, sodium perborate monohydrate, sodium percarbonate and sodium dichloroisocyannurate. Chlorine dioxide ($ClO_2$) precursor compounds such as sodium hypochlorite can also be used as alkaline agents in applications such as cleansing operations.

Therefore, the present invention also provides for a hydrostatic delivery system wherein the hydrostatic pressure modulating agent comprises an expansion source, selected from the group consisting of a carbon-dioxide precursor, an oxygen precursor, and a chlorine dioxide precursor. Preferably, when the hydrodynamic polymer comprises a carbon dioxide precursor, oxygen precursor or chlorine dioxide precursor, the hydrodynamic polymer and the hydrostatic pressure modulating agent are present in a ratio from about 99:1 to about 50:50 by weight, preferably, from about 99:1 to about 70:30 by weight.

As used herein, the term "acidic agent" refers to any compound or material that can serve as a proton source and can react with the alkaline agent of the invention to form a gas. The acidic agent can have more than one acid functional group, that is, more than one dissociation constant. The acidic agent can be any organic or inorganic acid in the free acid, acid anhydride and acid salt form. Preferably, the acidic agent is in a solid state at ambient temperatures, is not harmful to animals including man, and exhibits a pH of about 4.6 or lower when saturated into water at room temperature. Also included as acidic agents are acid alkali metal salts (e.g. sodium salt, potassium salt, etc.).

Examples of an acidic agent include, but are not limited to, citric acid, tartaric acid, fumaric acid, maleic acid, malic acid, lactic acid, succinic acid, adipic acid, glycolic acid, alpha hydroxy acids, ascorbic acid, amino acids and their alkali hydrogen acid salts, as well as alkali acid metal salts of acid substances such as phosphoric acid and pyrophosphoric acid or other inorganic acids provided those salts are solid at room temperature. The preferred type of acidic agent possess a relatively large acid dissociation constant ($10^3$ or more ) and a low hygroscopicity (critical humidity at 30° C. is 40% RH or more).

The ratio of the acidic agent and alkaline agent can be determined according to the amount of gas required to effect a desirable hydrostatic pressure. When the two compounds, i.e. the acidic and alkaline agents, are mutually reactive, it is preferable, although not necessary, that they react completely. Therefore, a ratio of components that provides for equal amounts of reaction equivalents is preferred. For example, if the acid used is diprotic, then either twice the amount of a mono-reactive carbonate alkaline agent, or an equal amount of all-reactive alkaline agent should be used for complete neutralization. The amount of alkaline agent can be increased if it is desired to increase the hydrostatic pressure of the delivery system. If the alkaline agent is a carbon dioxide precursor, the amount of the precursor within the delivery system varies from about 0.5 to about 70 weight %, preferably 2 to about 30 weight %, of the formulation. Preferably the acidic agent and a alkaline agent, for example a carbon dioxide precursor, are solid, for example in a powdery or granular state.

The hydrostatic couple as described herein, comprises a mixture of at least one group-A, hydrodynamic boundary compound, and at least one group-B, hydrostatic pressure-modulating agent. The combination thus formed is capable of establishing a positive hydrostatic differential pressure against the fluid environment.

The ratio of the group-A and group-B compounds in the hydrostatic couple is determined according to the amount of hydrostatic pressure required to produce a desired volume efflux. This ratio is also related to the hydrostatic pressure required to reach equilibrium "steady state" volume for the delivery system. The amount of hydrostatic couple in a particular delivery system will depend on the saturation solubility of the agent of interest to be delivered, the desired rate and the duration of such release from the delivery system.

The rate of release of the agent of interest may be selected considering several variables, for example, but not limited to the solubility of the agent of interest, and pharmacological activity of the agent of interest. For example, with decreased solubility or a low pharmacological activity, of an agent of interest, a faster release of the agent from the hydrostatic couple may be desired. Likewise, with a soluble agent of interest, or an agent that exhibits a high degree of pharmacological activity, a slower release of the agent from the delivery system may be desired, for example, but not limited to, using a hydrostatic couple as provided in Formula 2. It is to be understood, however, that the formulation of the hydrostatic couple may be varied as required to obtain a desired rate of release of an agent of interest.

The present invention also provides for a delivery system that utilizes capillarity as a means of fluid imbibition, and differential volume expansion of the hydrostatic couple to create a non-osmotic hydrostatic pressure. The resultant hydrostatic pressure produces the driving force for the controlled release of the agent of interest. The hydrodynamic boundary polymers of the hydrostatic couple, for example the group-A component(s), create a hydrodynamic boundary which is capable of moving, and is in dynamic equilibrium with, the components of the hydrostatic couple.

A further aspect of the present invention provides for a solid pharmaceutical dosage form, for example, but not limited to a matrix compact suitable for oral administration wherein the delayed release is brought about by use of suitable excipients that are industrially available, non-toxic and easy to process. The pharmaceutical dosage form includes, for example, but not limited to, compressed tablets, granules, pellets, suspensions, extrusion spheroids or compacts obtained by direct compression, wet granulation, dry granulation, hot melt granulation, microencapsulation, spray drying, and extrusion methods as would be evident to one of skill in the art. Other solid dosage forms such as hard gelatin capsules can also be derived from dry blends, granulations, suspensions, spheroids, pellets, tablets and combinations therefrom, as are commonly known in the art.

The pharmaceutical dosage form may also include excipients as required, for example, but not limited to, viscosity enhancer(s), enteric polymer(s), pH-specific barrier polymer(s), diluent(s), anti-adherent(s), glidant(s), binder(s), solubilizer(s), channeling agent(s), wetting agent(s), buffering agent(s), flavorants, adsorbents, sweetening agent(s), colorant(s) and lubricant(s):

The dosage forms and delivery system taught herein may be used in pharmaceutical, veterinary, food, pesticidal, horticultural, herbicidal, agricultural, cosmetic, industrial, cleansing, and confectionery applications.

Formulations incorporating the solid dosage forms can further include one or more additional adjuvants, which can be chosen from those known in the art including flavors, colors, diluents, binders, plasticizers, fillers, surfactant, solubilizers, stabilizers, compaction enhancers, channeling agents, glidants, lubricants, coating polymers and anti-adherents.

Hydrostatic Delivery System

When the hydrostatic delivery system of the present invention comes into contact with an external fluid of the environment, such as water or other biological fluid, the water of fluid is imbibed into the core of the delivery system in part by capillary hydration due to the hydrostatic couple. The volume of the hydrodynamic boundary, group-A components of the system increases due to a net inflow into the polymer structure. Concurrently, the rapidly expanding hydrostatic-pressure modulating agent (group-B component) also increases in volume. However due to the differential rates and extents of volume increase of the individual polymers, a positive differential hydrostatic pressure builds up within the delivery system. An expansion source also exerts pressure against the polymeric micropores of the cross-linked group-A polymer and thus produces a net differential pressure. The differential fluid pressure therefore is in part derived from the hydrostatic couple typically arising from the net effect of two dynamically independent processes contributed by each component of the couple.

Without wishing to be bound by theory, at a given point of net imbibed water, there is a given ratio of the number of hydrated group-A particles and expanded particles or molecules of the rapid expansion-group-B particles, that creates a positive differential pressure. This hydrostatic pressure acts against the influx of water and at some point the inflow of water will equal the outflow of water. The resultant hydrostatic volume efflux overwhelms the passive diffusive volume efflux within the delivery system. When the inflow and outflow of water become equal, the system manifests a dynamic constant volume and surface area. This results in a steady state release of solved or partially solved particles of the agent of interest along with any other adjuvant.

Without wishing to be bound by theory, the kinetics of volume fluxes due to the hydrostatic couple may be explained as follows: Upon contact with an external fluid, due to surface tension of the liquid and surface free energy at the solid-liquid interface, the liquid wets the pores of the hydrostatic couple components. Fluid enters into the porous structure of the components due to hydrostatic capillary action and surface tension. This imbibition continues so long as there is a pressure difference as a result of density differences between the imbibed liquid and the vapor (or air) within the solid polymer network of the hydrostatic couple. Therefore water inflow will continue until all solid components and polymer pores have been hydrated.

The volume influx from capillary action (k), leading to volume increase is $(dV/dt)_k$. This rise in volume is opposed by the diffusive flux, $(dM/dt)_d$, due to chemical potential gradient of dissolved solutes or agent of interest, and is driven by passive diffusion. The diffusive flux $(dM/dt)_d$, is equal to the product of the passive volume efflux and the concentration (C) of the solute; $(dV/dt)C_e$. In the absence of the hydrostatic pressure modulating agent(s), the net volume flux $(dV/dt)_T$. is given by the following equation (equation 1):

$$dV/dt_T = dv/dt_K - [dV/dt \times C]_e \qquad \text{Equation 1:}$$

The rate of volume influx is substantially greater than the diffusive rate of efflux, thus a constant volume increase is observed (see FIG. 1).

In the hydrostatic delivery system of this invention, the presence of a hydrostatic couple creates a positive hydrostatic pressure within the delivery system as a result of the differential rates of volume expansion between the group-A and group-B components. This differential pressure opposes the volume influx of the imbibed fluid and reduces the volume gain of delivery system. The volume efflux due the hydrostatic pressure $(dV/dt)_h$, is substantially greater than the contribution to volume efflux as a result of passive diffusive flux. At an optimal level, which may be determined by a mathematically predictable ratio of the components of the hydrostatic couple, the rate of volume efflux approaches and eventually equals the rate of volume influx. This represents a dynamic steady state with a zero net increase in volume and a constant surface area of the delivery system (see FIG. 2). The one or more agents of interest that are dissolved or partially solved within the delivery system, are thus released at a rate determined by the total (net) efflux controlled and determined by hydrostatic pressure within the delivery system. The insignificance of the passive diffusive contribution to the net volume efflux proffers a delivery system whose performance is independent of the chemical concentration gradient of the agent of intrest. If the volume within the delivery system is such that the total concentration of the agent of interst is above its saturation concentration, the resultant release of the agent of interest will exhibit a zero or near zero order kinetics. The net volume flux in the hydrostatic delivery system is represented by the following equation (equation 2):

$$\frac{dV}{dt_T} = \frac{dV}{dt_K} - \left[\frac{dV}{dt_h} + \frac{dV}{dt_d} \times C\right]_e \qquad \text{Equation 2}$$

$$\frac{dV}{dt_T} = \frac{dV}{dt_K} - \left[\frac{dV}{dt_h} \times C\right]_e$$

Figure 2:
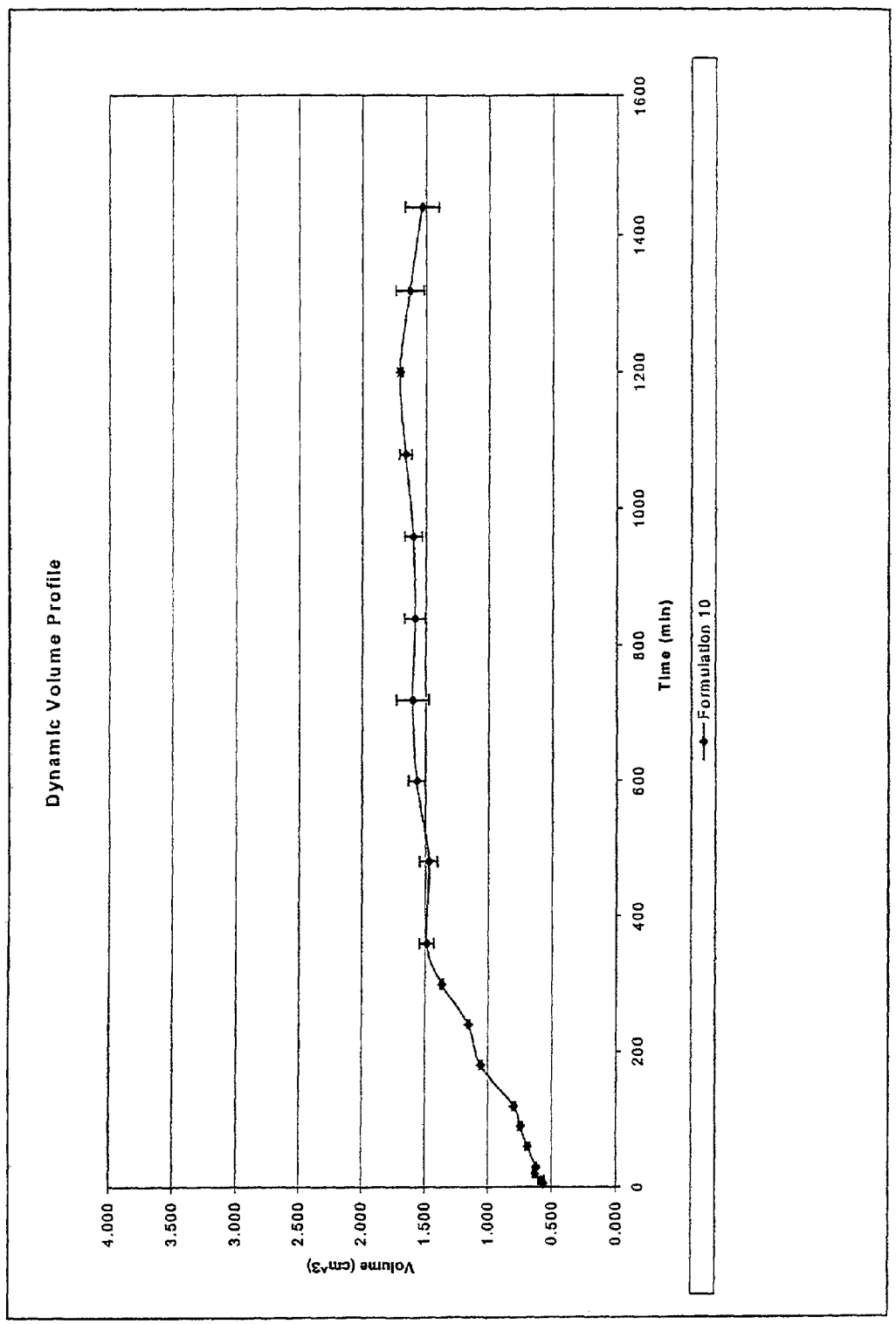
FIG. 2 shows the change in the dynamic profile of one formulation of a hydrostatic delivery system of the present invention.
Figure 4:
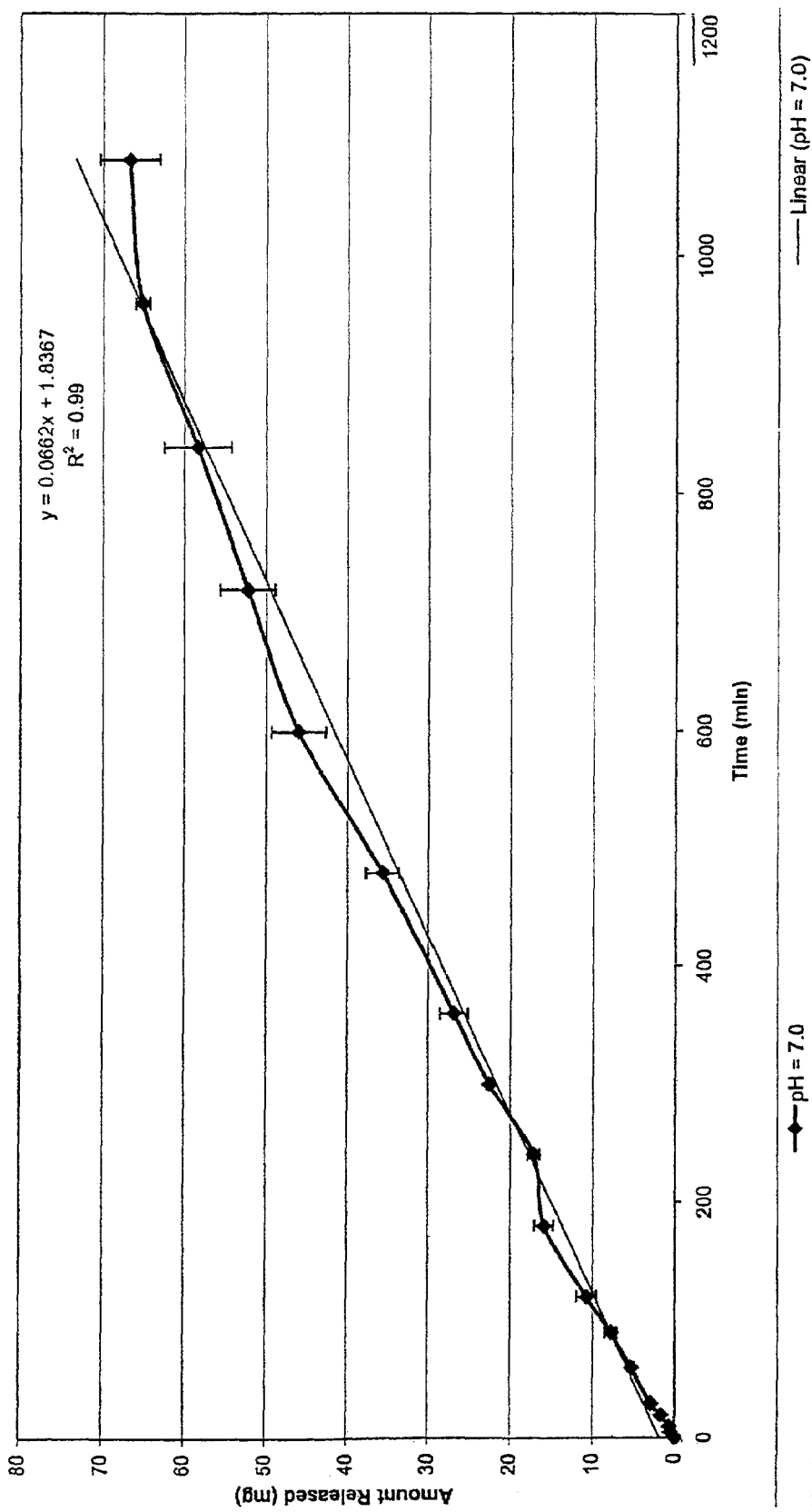
FIG. 4 shows the dissolution profile of the release of an agent of interest from the hydrostatic delivery system of the present invention exhibiting zero-order kinetics.
Figure 5:
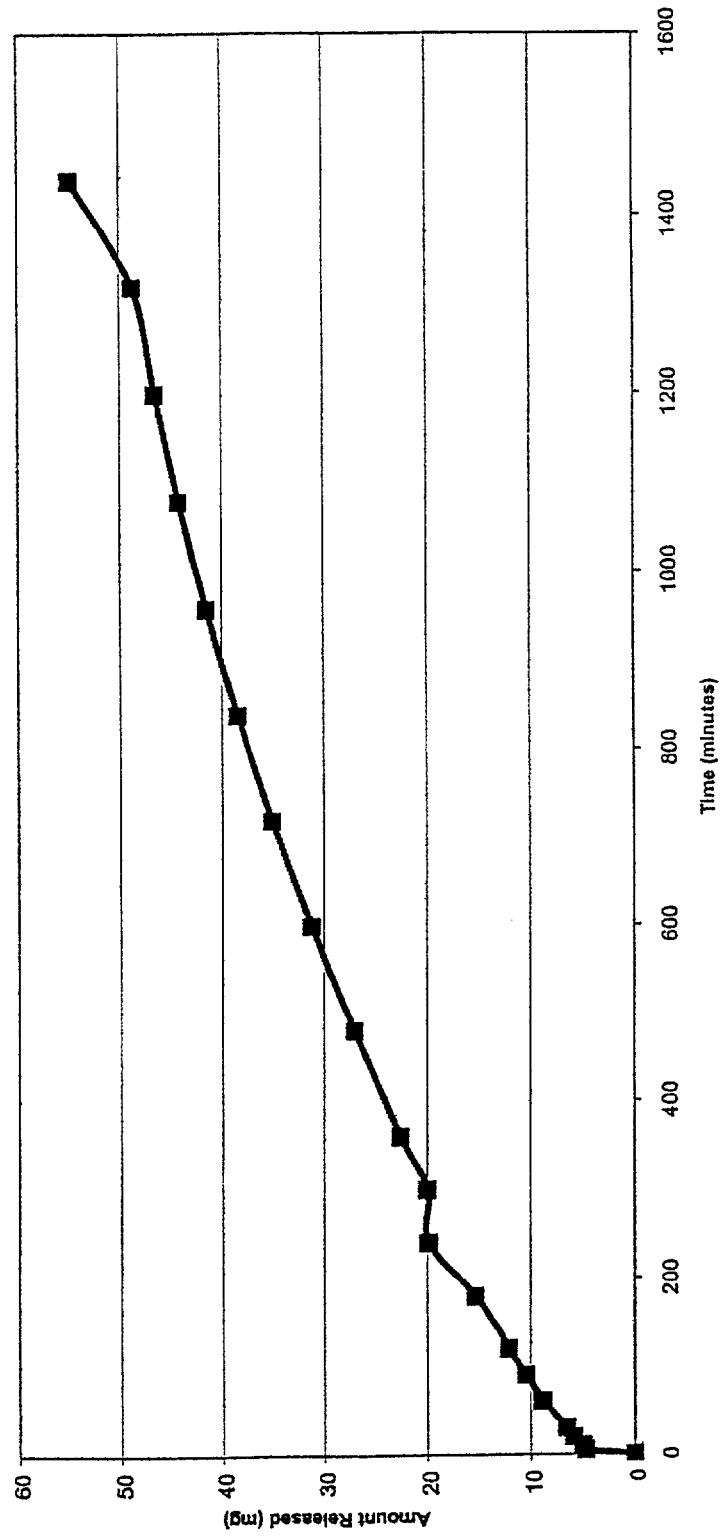
FIG. 5 shows the dissolution profile of the release of an agent of interest, Rantidine hydrochloride (60 mg) from the hydrostatic delivery system of the present invention exhibiting zero-order kinetics.
Figure 6:
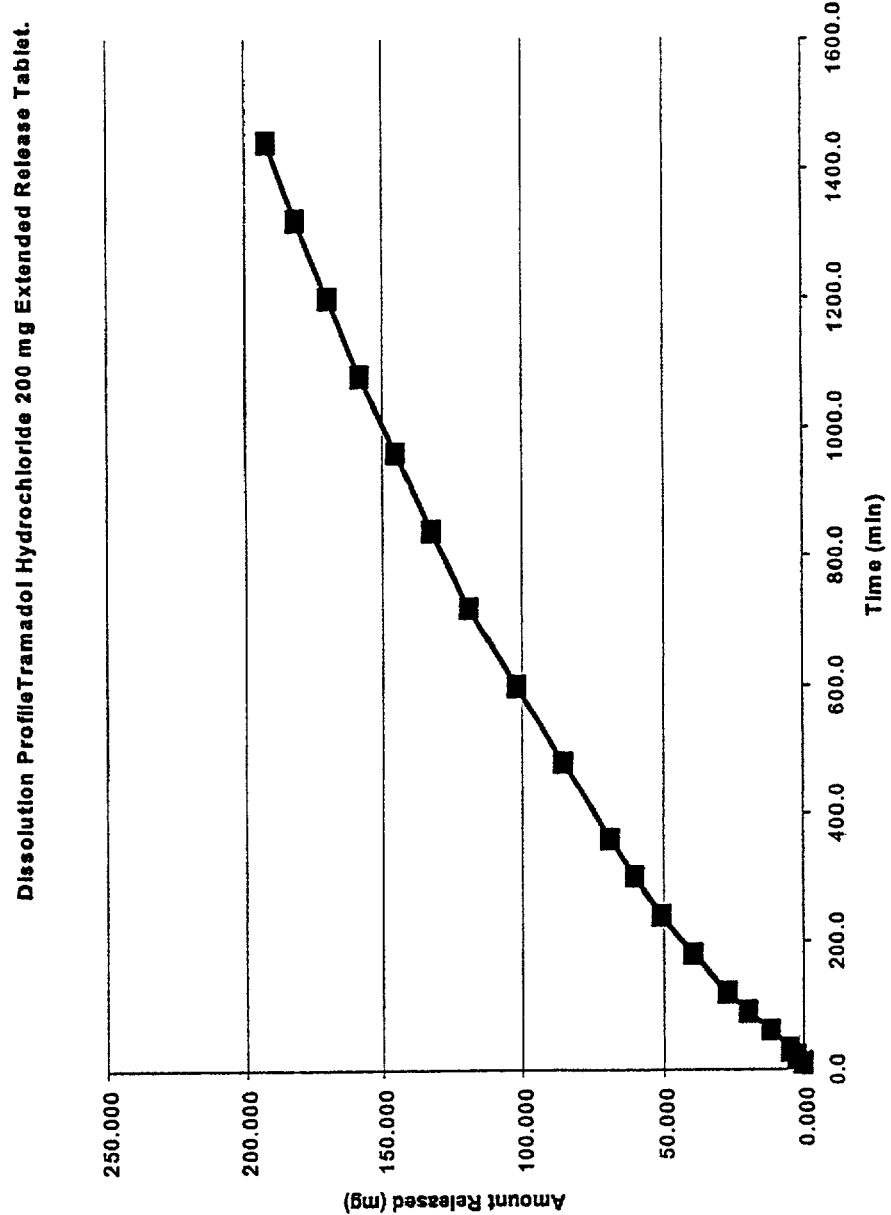
FIG. 6 shows the dissolution profile of the release of an agent of interest, Tramadol hydrochloride (200 mg) from the hydrostatic delivery system of the present invention exhibiting zero-order kinetics.

The dynamic fluid profile of a delivery system of the present invention comprising a hydrostatic couple as described herein is presented in FIG. 2. Following an initial increase in the dynamic volume of the tablet, the volume remains stable over time wherein the influx of fluid is equal to the efflux of caffeine. This represents a controlled increase in the dynamic profile of a tablet, which reaches and maintains a maximum volume after a period of time (depending upon the ratio of the hydrodynamic fluid-imbibing polymer, to hydrostatic pressure modulating agent). FIGS. 4-6 show a corresponding drug release (dissolution profile) for a range of formulations comprising a hydrostatic couple of the present invention and a range of concentrations of active ingredients. The dissolution profiles shown in FIGS. 4-6 each display a linear, zero-order release of an agent of interest for over 16 hours.

The above description is not intended to limit the claimed invention in any manner, furthermore, the discussed combination of features might not be absolutely necessary for the inventive solution.

The present invention will be further illustrated in the following examples. However it is to be understood that these examples are for illustrative purposes only, and should not be used to limit the scope of the present invention in any manner.

EXAMPLES

Example 1

Preparation of Hydrostatic Couple

The hydrostatic couple is prepared either by dry screening the components of group-A and group-B compounds followed by geometric blending of components to form an intimate mixture, or granulating the components to form discrete aggregates. The agent of interest is prepared and combined with the hydrostatic couple. This may be achieved by blending or further re-granulation to homogeneity. The resulting mixture is compressed on a B or D type tablet press to form a compact. Such compacts may be further coated if desired using standard techniques as known within the art.

A manufacturing process for a hydrostatic delivery system in form of a matrix tablet involves the following general steps:
a) Preparation of group-A component(s);
b) Preparation of group-B component(s);
c) Preparation of agent of interest formulation;
d) Blending a)-c);
e) Compressing the blend into a suitable compact;
f) Coating the compact with a suitable polymer.

Preparation of Group-A Granules

Granulate the selected item(s) of group-A component with 100% Isopropyl alcohol or suitable granulating fluid in a high-shear mixer-granulator. Wet screen in an Oscillating Granulator or suitable granulator equipped with mesh # 16 or # 20 or other suitable size. Dry the wet screened moist granules in a convection oven set at room temperature for 60-90 minutes. Dry screen in a Comill or suitable dry granulator (mesh 0.5-mm, 200-250 rpm). Dry further at 30-35° C. for 3-4 hours. Sieve in a Rotap for 3-4 minutes (screen # 60/100).

Preparation of Group-B Granules

Granulate the selected item(s) of group-B component with 100% Ethanol or other suitable solvent in a high-shear mixer-granulator. Wet screen in an Oscillating Granulator or suitable granulator equipped with mesh # 16 or # 20 or other suitable size. Dry the wet screened moist granules in a convection oven set at 30-35° C. for 90-120 minutes. Sieve in a Rotap for 3-4 minutes (screen # 16/60).

Preparation of Active Component Blend Comprising an Agent of Interest

The active compound blend may be prepared using any suitable method as would be known to one of skill in the art for example those disclosed in Lachman et al. (The Theory and Practice of Industrial Pharmacy, by L. Lachman, H, Lieberman and J. Kang. $3^{rd}$ Edition, Lea & Febiger 1986). This may involve combination of the agent of interest with an excipient, or granulation, or microencapsulation or other suitable method.

Blending & Compressing

Group-A and group-B granules are unifomly blended by geometric dilution in a Paterson-Kelly (PK) twin shell blender. After discharge, the active component blend is serially mixed with the blend composition of group-A and group-B components for about 6-8 minutes. The final composition is discharged and compressed into a suitable sized compact.

Coating

If desired, the compressed compact may be coated with an aqueous or solvent based polymer solution. The choice of polymer, solvent and plasticizer may vary as required and it is dependent on the desired outcome. The polymer may be a functional coating such as a pH-dependent enteric polymer or a non-functional coating such as a hydrosoluble polymer for esthetics.

Example 2

Two drug delibery systems were prepared in order to compare the dinetics of drug release and changes in dynamic bolume profile of the delibery system (tablet). The control comprised a prior art formulation, (Prior Art, Table 1) and the second delivery system comprised the hydrostatic couple (components listed in Table 1) as prepared using the method of Example 1. The agent of interest in bothe delibery systems was caffeine.

TABLE 1

Components of Prior art and hydrostatic couple formulations

| Component | Component | Amount per tablet (mg) |
|---|---|---|
| Prior art | | |
| Active agent | Caffeine Anhydrous USP | 160 |
| Control Release polymer | Carbopol 971P USP/NF | 224 |
| Flow Promoter | Colloidal Silicon Dioxide | 12 |
| Lubricant | Magnesium Stearate | 4 |
| Hydrostatic couple | | |
| Active agent | Caffeine Anhydrous USP | 70 |
| Hydrostatic couple | | |
| Group-A | Carbopol 971P | 280 |

Blending & Compressing

Group-A and group-B granules are unifomly blended by geometric dilution in a Paterson-Kelly (PK) twin shell blender. After discharge, the active component blend is serially mized with the blend composition of group-A and group-B components for about 6-8 minutes. The final positon is discharged and compressed into a suitable sized compact.

Coating

If desired, the compressed compact may be coated with an aqueous or solbent based polymer solution. Thew choice of polymer, solvent and plasticizer may vary as required and it is dependent on the desired outcome. The poymer may be a functional coating such as a pH-dependent enteric polymer or a non-fuctional coating such as a hydrosoluble polymer for estherics.

Example 2

Two drug delivery systems were prepared in order to compare the kinetics of drug release and changes in dynamic volume profile of the delivery system (tablet). The control comprised a prior art formulation, (Prior Art, Table 1) and the second delivery system comprised the hydrostatic couple (components listed in Table 1) as prepared using the method of Example 1. The agent of interestin both delivery systems was caffeine.

TABLE 1

Components of Prior art and hydrostatic couple formulations

| Component | Component | Amount per tablet (mg) |
|---|---|---|
| Prior art | | |
| Active agent | Caffeine Anhydrous USP | 160 |
| Control Release polymer | Carbopol 971P USP/NF | 224 |
| Flow Promoter | Colloidal Silicon Dioxide | 12 |
| Lubricant | Magnesium Stearate | 4 |
| Hydrostatic couple | | |
| Active agent | Caffeine Anhydrous USP | 70 |
| Hydrostatic couple | | |
| Group-A | Carbopol 971P | 280 |
| Group-B | Crospovidone XL-10 | 8 |
| Flow promoter | Colloidal Silicon Dioxide | 4.3 |
| Lubricant | Magnesium Sterate | 3.67 |

The prepared delivery systems were placed within PBS at pH 7.0 in a Type II USP 24 Dissolution apparatus at 37° C. (±0.5) using a paddle speed of 50 rpm. Caffeine release from the delivery systems were measured over time. Caffeine release was determined spectrophotometncally @ 272 nm.

Method for Measuring Synamic Volume Change Due to Fluid Imbibition

The dynamic volume change of a fluid-imbibing or swelling tablet was measured by computation of the density of the swollen tablet and its mass. The basic relationship is:

$$Vt = Mt/D$$

Where Vt is the volume at a given time; Mt, is the mass of swollen tablet at a given time; and D, is the density of the swollen tablet.

To obtain dynamic volume values, the same tablet undergoing swelling in the fluid media was removed from the dissolution media at regular (pre-fixed) time intervals, weighed in air (to obtain its mass) and weighed submerged in the fluid media (to obtain its buoyancy). The tablet is immediately returned to the dissolution media where swelling resumes. The time lapse between removal from the fluid media and its return to the media is kept constant and short in orderto minimize errors due to excessive dehydration. This time interval is typically not more than 30 seconds.

The density of the swolien tablet is obtained by calculating:

$$\rho 2 = (A/P) * \rho o$$

where, $\rho 2$ is the density of the swollen tablet; $\rho o$ is the density of the fluid media.

Equipment & Materals for Dynamic Volume Measurement
  Swelling & Drug Dissolution Measurements
  USP Dissolution Appaatus Type II (Paddle)
  Settings: Rotational Speed: 40-50 rpm
  Temperature: 37° C.+/−0.5° C.

PBS buffer pH 7.00 (or suitable buffer at a desired pH).

Dynamic Volume Measurements
  Merler-Taledo Density Determination Kit (forliquids and Solids) Model #33360
  Media: PBS buffer pH 7.00 or suitable buffer at a desired pH.

Figure 3:
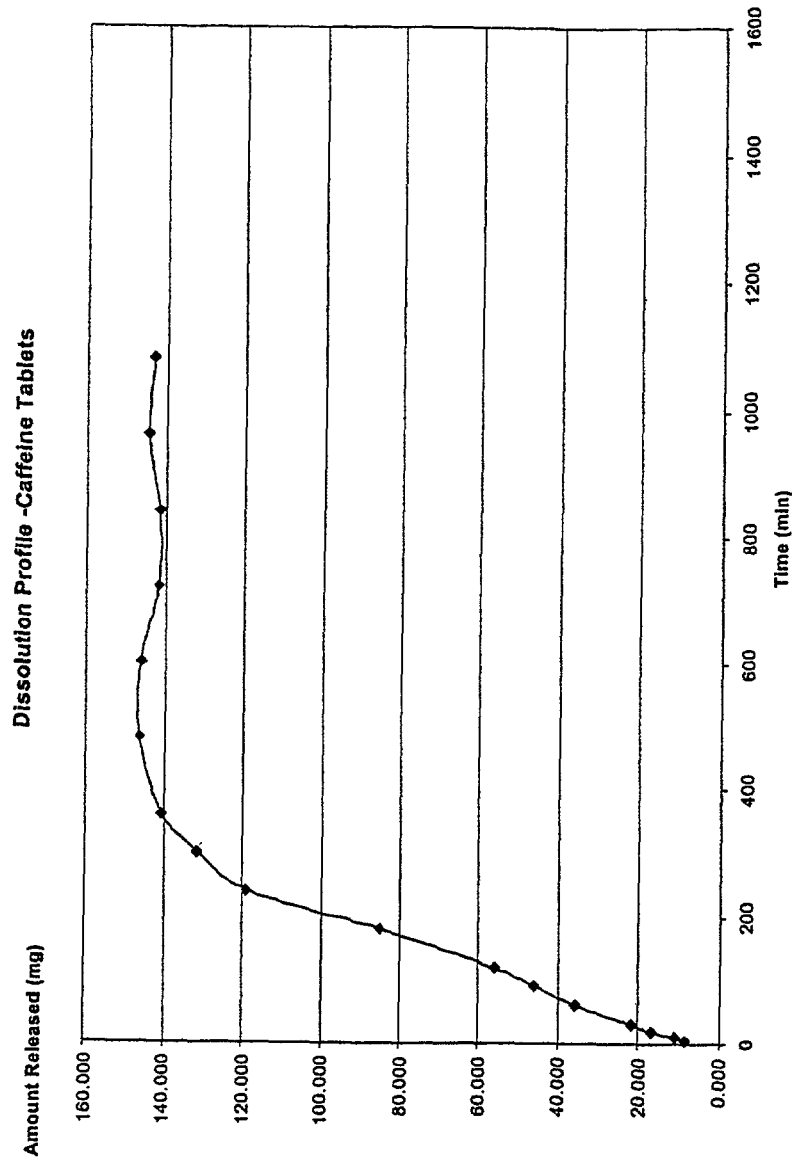
FIG. 3 shows the dissolution profile of the release of an agent of interest from the hydrostatic delivery system of the prior art exhibiting non-zero (exponential) kinetics.

FIG. 1 shows a plot of the dynamic volume profile of a prior art formulation, demonstrating a linear volume increase associated with a hydrodynaic polymer (Group-A component). The corresponding drug release (dissolution profile) for this formulation is shown in FIG. 3. A rapid release (exponential) of an agent of interest from the prior art delivery system, reaching a maximum release rate after about 3.5 to 4 hours is evident in FIG. 3. This is the typical Fickian release manifested by prior art compositions using group A-type components as the control release polymer. With This delivery system, the rate of efflux of an agent of inerest is due to passive diffusion and is substantially less than the rate of influx of the fluid. Consequently, the rate of release of an agent of interest is dependant on the chemical potential and concentration of the agent.

The dynamic fluid profile of a delivery system of the present invention comprising a hydrostatic couple provided in Table 1 is presented in FIG. 2. Following an initial increase in the dynamic volume of the tablet, the volume remains stable over

Example 4

Extended Release Nifedipine 60 mg

TABLE 3

Extended Release Nifedipine

| Components | Formula-1 | Formula-2 |
|---|---|---|
| Nifedipine USP | 60.00 mg | 60.00 mg |
| Carbopol 971P NF | 171.00 mg | 171.00 mg |
| Carbopol 934P NF | 9.00 mg | 9.00 mg |
| Crospovidone XL-10 | 3.60 mg | 0.00 mg |
| Crosphovidone INF-10 | 0.00 mg | 3.60 mg |
| Cyclodextrin NF | 2.00 mg | 2.00 mg |
| Sodium Lauryl Sulphate | 1.50 mg | 1.50 mg |
| Colloidal Silicon Dioxide NF | 3.00 mg | 3.00 mg |

Example 5

Extended Release Diltiazem 60 mg

TABLE 4

Extended Release Diltiazem

| Components | Formula-1 | Formula-2 |
|---|---|---|
| Diltiazem USP | 60.00 mg | 60.00 mg |
| Carbopol 971P NF | 171.00 mg | 171.00 mg |
| Crospovidone XL-10 | 3.60 mg | 0.00 mg |
| Crospovidone INF-10 | 0.00 mg | 3.60 mg |
| Cyclodextrin NF | 2.00 mg | 2.00 mg |
| Colloidal Silicon Dioxide NF | 3.00 mg | 3.00 mg |

Example 6

Extended Release Buspirone Hydrochloride 20 mg

TABLE 5

Extended Release Buspirone hydrochloride

| Components | Formula-1 | Formula-2 |
|---|---|---|
| Buspirone Hydrochloride USP | 20.00 mg | 20.00 mg |
| Carbopol 971P NF | 171.00 mg | 171.00 mg |
| Crospovidone XL-10 | 3.60 mg | 0.00 mg |

TABLE 5-continued

Extended Release Buspirone hydrochloride

| Components | Formula-1 | Formula-2 |
|---|---|---|
| Crospovidone INF-10 | 0.00 mg | 3.60 mg |
| Cyclodextrin NF | 2.00 mg | 2.00 mg |
| Colloidal Silicon Dioxide NF | 3.00 mg | 3.00 mg |

Example 7

Extended Release Rantidine Hydrochloride 60 mg

The preparation of an extended release formulation composition comprising Rantidine Hydrochloride (Table 6) was prepared as described herein (Example 1). The release of Ranitidine hydrochloride was measured in a USP dissolution apparatus type II dissolution apparatus under the following conditions:

Paddle speed: 50 rpm
Temperature: 37°C. (±0.5)
Media: PBS buffer pH 7.0
Volume: 900 ml
Sampling Duration: 24 hours.

Ranitidine hydrochloride release was determined spectrophotometrically @ 322 nm. The results for this experiment are shown in FIG. 5.

TABLE 6

Composition of Rantidine Hydrochloride Tablets

| Component | | Amount |
|---|---|---|
| Model drug Hydrostatic Couple | Ranitidine Hydrochloride | 60.00 mg |
| Group-A | Carbopol 971P | 203.66 mg |
| Group-B | Crospovidone XL-10 | 1.54 mg |
| Other excipients | | |
| Binder (pH sensitive) | Hydroxyl Propoyl Methyl Cellulose Phthalate | 4.00 mg |
| Lubricant | Magnesium stearate | 4.00 mg |

As shown in FIG. 5, the dissolution profile for Ranitidine Hydrochloride from a formulation comprising a hydrostatic couple of the present invention, displays a linear, zero-order release of an agent of interest for over 16 hours.

Example 8

Extended Release Tramadol Hydrochloride 200 mg

Extended release formulations comprising Tramadol hydrochloride (200 mg; composition outlined in Table 7) were prepared as described in Example 1. Extended release of Tramadol hydrochloride was measured in a USP dissolution apparatus type II dissolution apparatus under the following conditions:

Paddle speed: 50 rpm
Temperature: 37° C. (±0.5)
Media: PBS buffer pH 7.0
Volume: 900 ml
Sampling Duration: 24 hours Tramadol hydrochloride release was determined spectrophotometrically @ 275 nm. The results of this experiment are shown in FIG. 6.

TABLE 7

Composition of Tramadol Hydrochloride Tablets

| Component | | Amount |
|---|---|---|
| Model drug Hydrostatic Couple | Tramadol Hydrochloride | 200.00 mg |
| Group-A | Carbopol 971P | 200.50 mg |
| Group-B | Crospovidone XL-10 | 1.20 mg |
| Other excipients | | |
| Lubricant | Magnesium stearate | 2.00 mg |

The results shown in FIG. 6, demonstrate that the dissolution profile for Tramadol hydrochloride from a formulation comprising a hydrostatic couple of the present invention, displays a linear, zero-order release of an agent of interest for over 16 hours.

All citations are herein incorporated by reference.

The present invention has been described with regard to preferred embodiments. However, it will be obvious to persons skilled in the art that a number of variations and modifications can be made without departing from the scope of the invention as described herein.

The embodiments of the invention in which an exclusive property of privilege is claimed are defined as follows:

1. A dosage form for oral administration consisting of:
   a compressed homogeneous mixture comprising:
   a pharmacologically-active substance; and
   a hydrostatic couple consisting of:
   a) at least one crosslinked hydrodynamic fluid-imbibing polymer selected from the group consisting of:
      i) an acrylic-acid polymer cross-linked with allylsucrose or allylpentaerythritol;
      ii) one or more high amylose starches cross-linked by epichlorhydrin, phosphorous oxychloride (POCl$_3$), or sodium trimetaphosphate;
      iii) a crosslinked polylglucan;
      iv) a crosslinked polyethylenimine;
      v) a crosslinked polyallylamine, and
      vi) combinations thereof; and
   b) at least one crosslinked hydrostatic pressure-modulating agent selected from the group consisting of:
      i) a homopolymer of cross-linked N-vinyl-2-pyrollidone;
      ii) a rapidly expanding cross-linked cellulose derivative selected from the group consisting of cross-linked carboxymethyl cellulose, sodium starch glycolate, and combinations thereof; and
      iii) combinations thereof.

2. The dosage form of claim 1, wherein said crosslinked polyglucan is selected from the group consisting of amylose containing diester or diether crosslinks, dextran containing diester or diether crosslinks, pullulan succinate containing diester or diether crosslinks, pullulan glutarates containing diester or diether crosslinks, and combinations thereof.

3. The dosage form of claim 1, wherein the pharmacologically-active substance is selected from the group consisting of analgesics, anti-inflammatories, antimicrobials, amoebicidals, trichomonocidal agents, anti-Parkinson's, anti-malarials, anticonvulsants, anti-depressants, antiarthritics, anti-fungals, antihypertensives, antipyretics, anti-parasites, antihistamines, alpha-adrenergic agonists, alpha blockers, anesthetics, bronchial dilators, biocides, bactericides, bacteriostats, beta adrenergic blockers, calcium channel blockers, cardiovascular drugs, contraceptives, decongestants, diuretics, depressants, diagnostics, electrolytes, hypnotics, hormones, hyperglycemics, muscle relaxants, muscle contractants, ophthalmics, parasympathomimetics, psychic energizers, sedatives, sympathomimetics, tranquilizers, viricides, vitamins, non-steroidal anti-inflammatories, angiotensin converting enzyme inhibitors, polypeptides, proteins, and sleep inducers.

4. The dosage form of claim 1, wherein said at least one crosslinked hydrodynamic fluid-imbibing polymer has a swell capacity in a fluid environment of between about 1 weight % to about 3000 weight %.

5. The dosage form of claim 1, wherein said at least one crosslinked hydrostatic pressure-modulating agent is a rapidly swelling polymer having a swell capacity in a fluid environment of between about 0.5 weight % to about 500 weight %.

6. The dosage form of claim 1, wherein said pharmacologically-active substance is released in a controlled manner with zero-order or near zero-order release kinetics over a therapeutically practical time period following administration of said dosage form.

7. A dosage form for oral administration consisting of:
a compressed homogeneous mixture comprising:
  a pharmacologically-active substance; and
  a hydrostatic couple consisting of:
  a) at least one crossliniked hydrodynamic fluid-imbibing polymer selected from the group consisting of:
    i) an acrylic-acid polymer cross-linked with allylsucrose or allylpentaerythritol;
    ii) one or more high amylose starches cross-linked by epichlorhydrin, phosphorous oxychloride ($POCl_3$), or sodium trimetaphosphate;
    iii) a crosslinked polyglucan;
    iv) a crosslinked polyethylenimine;
    v) a crosslinked polyallylamine, and
    vi) combinations thereof; and
  b) at least one crosslinked hydrostatic pressure-modulating agent selected from the group consisting of:
    i) a homopolymer of cross-linked N-vinyl-2-pyrollidone;
    ii) a rapidly expanding cross-linked cellulose derivative selected from the group consisting of crosslinked carboxymethyl cellulose, sodium starch glycolate, and combinations thereof; and
    iii) combinations thereof; and
  c) an expansion source.

8. The dosage form of claim 7, wherein said expansion source is selected from the group consisting of a carbon-dioxide precursor, an oxygen precursor, and a chlorine dioxide precursor.

9. The dosage form of claim 8, wherein said carbon dioxide precursor is selected from the group consisting of carbonates, sesquicarbonate, hydrogen carbonate, potassium carbonate, lithium carbonate, sodium carbonate, ammonium carbonate, sodium amino acid carbonate, sodium glycine carbonate, L-lysine carbonate and arginine carbonate.

10. The dosage form of claim 8, wherein said oxygen precursor is selected from the group consisting of sodium percarbonate, sodium perborate monohydrate, anhydrous sodium perborate, effervescent perborate, and sodium dichloroisocyannurate.

11. The dosage form of claim 8, wherein said chlorine dioxide precursor is selected from the group consisting of sodium hypochlorite and calcium hypochlorite.

* * * * *

UNITED STATES PATENT AND TRADEMARK OFFICE
CERTIFICATE OF CORRECTION

PATENT NO. : 7,381,424 B2 Page 1 of 4
APPLICATION NO. : 10/006740
DATED : June 3, 2008
INVENTOR(S) : Alexander MacGregor It is certified that error appears in the above-identified patent and that said Letters Patent is hereby corrected as shown below:

Column 3, line 22, delete "therefore," and insert -- Therefore, --.

Column 8, line 1, delete "alpha." and insert -- α --;

Column 8, line 5, delete "17. alpha." and insert -- 17α --;

Column 8, line 6, delete "10. alpha." and insert -- 10α --;

Column 8, line 19, delete "beta." and insert -- β --;

Column 8, line 28, delete "B.sub. 12" and insert -- $B_{12}$ --;

Column 8, line 38, delete "alpha." and insert -- α --;

Column 8, line 45, delete "carboxylicacid" and insert -- carboxylic acid --;

Column 8, line 55, delete "carboxylicacid" and insert -- carboxylic acid --; and Column 8, line 61, delete "1 ,4" and insert -- 1,4 --.

Column 12, line 25, delete "Prefreably," and insert -- Preferably, --.

Column 16, line 33, delete "intrest" and insert -- interest --; and

Column 16, line 35, delete "interst" and insert -- interest --.

Column 18, delete lines 13 - 56 in their entirety; and

Column 18, line 66, delete "interestin" and insert -- interest in --.

Column 19, line 26, delete "Synamic" and insert -- Dynamic --;

Column 19, line 44, delete "orderto", and insert -- order to --;

Column 19, line 46, delete "swolien" and insert -- swollen --;

Column 19, line 52, delete "Materals" and insert -- Materials --;

Column 19, line 55, delete "Appaatus" and insert -- Apparatus --;

Column 19, line 61, delete "Merler-Taledo" and insert -- Mettler-Toledo --; and delete "forliquids" and insert -- for liquids --; and

UNITED STATES PATENT AND TRADEMARK OFFICE
CERTIFICATE OF CORRECTION

| | | |
|---|---|---|
| PATENT NO. | : 7,381,424 B2 | |
| APPLICATION NO. | : 10/006740 | |
| DATED | : June 3, 2008 | |
| INVENTOR(S) | : Alexander MacGregor | |

It is certified that error appears in the above-identified patent and that said Letters Patent is hereby corrected as shown below:

Column 19, line 67, delete "hydrodynaic" and insert -- hydrodynamic --.

Column 20, line 8, delete "This" and insert -- this --;

Column 20, line 9, delete "inerest" and insert -- interest --;

Column 20, line 17, after "over" insert the following: -- time wherein the influx of fluid is equal to the efflux of caffeine. This represents a controlled increase in the dynamic profile of a tablet, which reaches and maintains a maximum volume after a period of time (depending upon the ratio of the hydrodynamic fluid-imbibing polymer, to hydrostatic pressure modulating agent). Figure 4 shows the corresponding drug release (dissolution profile) for a formulation comprising a hydrostatic couple of the present invention, and displays a linear, zero-order release of an agent of interest for over 16 hours. Figures 2 and 4 demonstrate how the volume increase in a --.

Column 20, after line 17, insert the following paragraphs and table:
-- delivery system comprising a hydrostatic couple is reduced, resulting in an increased and continuous efflux rate. Because the rate of efflux of the agent of interest is independent on the concentration of the agent but dependent on the hydrostatic pressure within the delivery system, the kinetics of agent release is zero-order.

Examples 3-6:

In these examples hydrostatic delivery systems for extended release formulation of various therapeutic agents are presented. Two formulations (Formula 1 and Formula 2) are used to illustrate how the hydrostatic couple as described herein can be used to achieve zero-order kinetics and predictably different release rates. Formula 1 exhibits faster rates of drug release than that observed with Formula 2. The rate of release of the agent of interest may be selected considering several variables, for example, but not limited to the solubility of the agent of interest, and pharmacological activity of the

UNITED STATES PATENT AND TRADEMARK OFFICE
CERTIFICATE OF CORRECTION

PATENT NO. : 7,381,424 B2
APPLICATION NO. : 10/006740
DATED : June 3, 2008
INVENTOR(S) : Alexander MacGregor It is certified that error appears in the above-identified patent and that said Letters Patent is hereby corrected as shown below:

agent of interest. For example, with decreased solubility of an agent of interest, faster release of the agent may be desired such as that provided by, but not limited to, Formula 1. In the case of a soluble agent of interest, slower release of the agent from the delivery system may be desired, for example, but not limited to, using a hydrostatic couple as provided in Formula 2. It is to be understood, however, that the formulation of the hydrostatic couple may be varied as required to obtain a desired rate of release of an agent of interest.

Example 3
Extended Release Theophylline 80 mg

Table 2

Extended Release Theophylline

| Components | Formula-1 | Formula-2 |
|---|---|---|
| Theophylline USP | 80.00 mg | 80.00 mg |
| Carbopol 971P NF | 320.00 mg | 320.00 mg |
| Crospovidone XL-10 | 6.40 mg | 0.00 mg |
| Crospovidone INF-10 | 0.00 mg | 6.40 mg |
| Sodium Lauryl Sulphate NF | 4.00 mg | 4.00 mg |
| Colloidal Silicon Dioxide NF | 3.00 mg | 3.00 mg |

--.

UNITED STATES PATENT AND TRADEMARK OFFICE
CERTIFICATE OF CORRECTION

PATENT NO.        : 7,381,424 B2
APPLICATION NO. : 10/006740
DATED             : June 3, 2008
INVENTOR(S)       : Alexander MacGregor It is certified that error appears in the above-identified patent and that said Letters Patent is hereby corrected as shown below:

Column 21, line 23, delete "37 ⊕ C" and insert -- 37° C --.

Signed and Sealed this

Twenty-fourth Day of November, 2009

David J. Kappos
*Director of the United States Patent and Trademark Office*